United States Patent [19]

Turner

[11] 4,268,518
[45] May 19, 1981

[54] METHOD OF TREATING CYSTITIS
[75] Inventor: David M. Turner, Quorn, England
[73] Assignee: Fisons Limited, Suffolk, England
[21] Appl. No.: 147,497
[22] Filed: May 7, 1980
[30] Foreign Application Priority Data
  May 19, 1979 [GB] United Kingdom ............... 17483/79
[51] Int. Cl.³ ............................................. A61K 31/35
[52] U.S. Cl. .................................................... 424/283
[58] Field of Search ......................................... 424/283
[56] References Cited
  U.S. PATENT DOCUMENTS

| | | | |
|---|---|---|---|
| 3,686,412 | 8/1972 | Fitzmaurice et al. | 424/283 |
| 3,720,690 | 3/1973 | King et al. | 424/283 X |
| 3,777,033 | 12/1973 | Fitzmaurice et al. | 424/283 |
| 3,975,536 | 8/1976 | Stevenson et al. | 424/283 |
| 4,029,761 | 6/1977 | Kingsley | 424/283 X |
| 4,067,992 | 1/1978 | Kingsley et al. | 424/283 |
| 4,146,634 | 3/1979 | Brown et al. | 424/283 |
| 4,152,448 | 5/1979 | Wardell | 424/283 |

Primary Examiner—Frank Cacciapaglia, Jr.
Attorney, Agent, or Firm—Merriam, Marshall & Bicknell

[57] ABSTRACT

There is described a method of treatment of mammalian cystitis, which method comprises administration of a compound of the formula I,

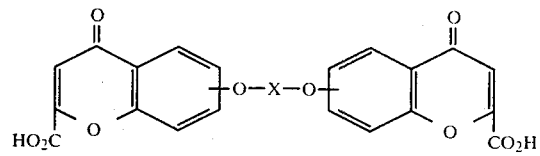

wherein X is a polymethylene chain containing 3 to 7 carbon atoms inclusive, which chain may be substituted by an —OH group, or a pharmaceutically acceptable salt, ester or amide thereof, to a patient having cystitis.

10 Claims, No Drawings

METHOD OF TREATING CYSTITIS

This invention relates to a new therapeutic method.

In U.S. Pat. No. 3,686,412 there are described a large number of bis-chromonyl compounds and their use in the treatment of asthma. These compounds are described as being administered preferably by way of inhalation.

Surprisingly we have now found that a selected group of these compounds are useful in the treatment of cystitis, and especially interstitial cystitis, a condition for which no adequate treatment is currently available.

According to the invention there is provided a method of treatment of mammalian cystitis, which method comprises administration of a compound of the formula I,

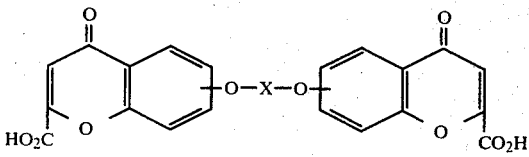

wherein X is a polymethylene chain containing 3 to 7 carbon atoms inclusive, which chain may be substituted by an —OH group, or a pharmaceutically acceptable salt, alkyl C 1 to 10 ester, mono-alkyl C 1 to 10 amide, di-alkyl C 1 to 10 amide or unsubstituted amide thereof, as active ingredient, to a patient having cystitis.

Suitable pharmaceutically acceptable salts include, for example, ammonium salts, alkali metal salts (e.g. sodium, potassium and lithium), alkaline earth metal salts (e.g. magnesium and calcium), and salts with organic amines (e.g. mono- di- or tri- alkyl C 1 to 6 amines, piperidine, and trialkanol C 1 to 6 amine salts). Esters which may be mentioned include simple alkyl esters (e.g. methyl, ethyl, propyl, isopropyl, butyl and tertiary butyl esters) and amides which may be mentioned include simple amides (for example amides with ammonia and lower alkylamines such as methylamine, ethylamine, etc.)

The administration may be oral, e.g. oesophageal, but is preferably by instillation into the bladder. Instillation into the bladder is particularly useful in the treatment of females.

The mammal to be treated is preferably a human.

In order to produce suitable compositions the drug is worked up with inorganic or organic pharmaceutically acceptable adjuvants, carriers or excipients. Examples of such adjuvants are:

For tablets and dragées: Binders, for example, cellulosic materials, e.g. microcrystalline cellulose and methyl cellulose; disintegrating agents, for example starches, e.g. maize starch; stabilizers, e.g against hydrolysis of the active ingredients; flavouring agents, for example sugars such as lactose; fillers; stearates and inorganic diluents, e.g. talc.

For syrups, suspensions, dispersions or solutions, e.g. for instillation: A liquid vehicle in which the active ingredients may be dissolved or suspended, e.g. water; and suspending agents, e.g. cellulose derivatives, gums etc. We prefer to use sterile aqueous solution containing from 0.05 to 10% w/w and preferably from 0.5 to 5% w/w, e.g. 1, 2 or 4%, of an active ingredient for instillation. For instillation into the bladder a dosage of about 50 to 150 ml, e.g. 100 ml, of solution is in general appropriate.

For hard or soft capsules: Diluents, e.g. lactose; glidants, e.g. stearates; inorganic materials, e.g. silica or talc; stabilisers and dispersing agents.

The composition may also contain further adjuvants, for example a composition for use in tablets may contain lubricants and glidants to assist in tableting, e.g. magnesium stearate, or wetting agents to assist in granulation, e.g. dioctyl sodium sulphosuccinate. The composition may also if desired contain a pharmaceutically acceptable dye or colourant, and may, if desired, be coated using conventional film or sugar coating techniques.

If desired the composition may be formulated in sustained release form, e.g. by coating the drug particles themselves, or granules thereof made with, for example, sucrose, and of a size up to 2 mm in diameter with a layer of, e.g. beeswax, Carnauba wax, stearic or palmitic acids, cetyl alcohol or similar substances which could be expected to be slowly dissolved or digested or to act as semi-permeable membranes through which drug can diffuse when the preparations are ingested. The composition may contain drug particles or granules which are uncoated in admixture with particles or granules having one or more coats of the coating medium, and may be in the form of a capsule containing the particles or granules or alternatively a tablet, for which other adjuvants may be required, such as glidants or lubricants. The drug may be administered as an enteric coated composition to make the drug available at the appropriate part of the gastro-intestinal tract. This may be achieved by coating the tablet with a continuous film of material which is resistant and impermeable to gastric secretions, but which is susceptible to intestinal secretions. Typical film materials are shellac and its derivatives and cellulose acetate phthalate.

The drug may, if desired, by used in a specific form, e.g. having a mass median diameter of less than 10 microns.

The drug may also be formulated as an aqueous, e.g. a water: chloroform (400:1), solution containing from 0.001 to 10.0% by weight of the drug. The free acids of formula I may conveniently be administered as an aqueous suspension containing from 0.01 to 10%, e.g. about 2% by weight of the drug.

The dosage to be administered will of course vary with the method of administration, the condition to be treated, its severity and with its location. However in general a dosage of from about 100 to 5,000, preferably 250 to 4,000 more preferably 500 to 3,000, and most preferably 1,000 to 2,000 mg of the drug administered to 1 to 8 times a day (i.e. a daily dosage of 100 to 40,000 mg) is found to be satisfactory. We also provide a method in which the dosage is from 500 to 2,000 mg of the drug administered 2 to 6 times, and preferably 2 to 4 times a day. Liquids should preferably not be taken by the patient for 2 hours before to 2 hours after administration of the instilled drug. Continuous or intermittant instillation may be used.

Conditions which may be treated by the method of our invention include cystitis in general and interstitial cystitis (or Hunner's ulcer) in particular, especially interstitial cystitis in women, e.g. women aged over 40. Administration by instillation may be trans-urethral or trans-vesical administration.

Specific examples of the group X are groups of the formula —(CH$_2$)$_5$— and —CH$_2$CHOHCH$_2$—.

The chain —O—X—O— may link different or corresponding positions on the chromone nuclei.

A specific compound which may be used in this invention is 1,3-bis(2-carboxychromon-5-yloxy)-2-hydroxy-propane.

This compound may of course be used in the form of its pharmaceutically acceptable, e.g. its di-sodium, di-potassium, calcium, magnesium or di-piperidine salt. It may also be used in the form of its di-ethyl ester, or of its simple amide derived from ammonia.

The invention is illustrated, but in no way limited by the following Examples.

EXAMPLE 1

The experiment was designed to test the effect of different concentrations of the di-sodium salt of 1,3-bis(2-carboxychromon-5-yloxy)-2-hydroxypropane (Compound A) on normal rat bladders and on rat bladders in which cystitis had been induced with Cetavlon (ICI). An epidural catheter was passed into the rat bladder per urethram and the bladder emptied. The bladder was then filled with a solution of Compound A or Cetavlon and the solution left in the bladder for 30 minutes. In some animals Cetavlon was introduced prior to Compound A and in the reverse order in others. Some animals were sacrificed immediately; others were allowed to recover and sacrificed at 7 days. In the event of death before this time, autopsy was performed. All bladders were examined histologically after staining with haematoxylin and eosin, and Von Gieson's stains.

Compound A at concentrations of 1% and 2% had no histologically discernible effects on the rat bladders studied. Instillation of Compound A prior to the Cetavlon induction of cystitis appeared to have protective properties in that the inflammatory response was milder.

EXAMPLE 2

Method 100 ml of 1% aqueous solution of Compound A were instilled once daily for 12 days into the bladders of 2 women aged between 40 and 60 both suffering from interstitial cystitis. This volume does not distend the bladder unduly. Patients were seen and cystoscoped at 4 weeks.

Results

The two patients responded to therapy. The patients noticed an improvement in symptoms 4–5 days after the course of treatment was completed. The following more detailed observations were made:

Patient 1

Symptomatic relief after day 16 (approx).
Cystoscopy negative at 4 weeks.
Biopsy negative at 4 weeks.
Patient relapsed at 6 weeks.

Patient 2

Apparent cure.
Cystoscopy negative at 4 weeks.
Biopsy negative at 4 weeks.
No relapse thus far (6 weeks.)

Haematological and biochemical parameters remained unchanged in both patients.

I claim:

1. A method of treatment of mammalian cystitis, which method comprises oral administration or instillation into the bladder of an effective amount of a compound of the formula I,

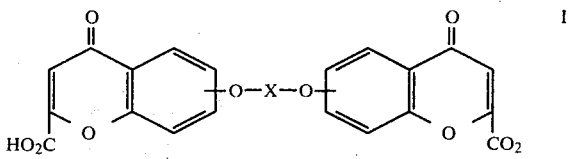

wherein X is a polymethylene chain containing 3 to 7 carbon atoms inclusive, which chain may be substituted by an —OH group,
or a pharmaceutically acceptable salt, alkyl C 1 to 10 ester, mono-alkyl C 1 to 10 amide, di-alkyl C 1 to 10 amide or unsubstituted amide thereof, as active ingredient, to a patient having cystitis.

2. A method according to claim 1, wherein the active ingredient is instilled into the bladder.

3. A method according to claim 1, wherein the active ingredient is instilled into the bladder as a sterile aqueous solution containing from 0.05 to 10% w/w of active ingredient.

4. A method according to claim 3, wherein the aqueous solution contains from 0.5 to 5% w/w of active ingredient.

5. A method according to claim 3, wherein from 50 to 150 ml of solution is instilled into the bladder.

6. A method according to claim 1, wherein the cystitis is interstitial cystitis.

7. A method according to claim 6, wherein the patient is a woman.

8. A method according to claim 1, wherein the active ingredient is 1,3-bis(2-carboxychromon-5-yloxy)-2-hydroxypropane or a pharmaceutically acceptable salt thereof.

9. A method according to claim 1, wherein the active ingredient is the disodium salt of 1,3-bis(2-carboxychromon-5-yloxy)-2-hydroxypropane.

10. A method according to claim 1, wherein from 100 to 5,000 mg of active ingredient is administered to the patient.

* * * * *